US006709311B2

(12) United States Patent
Cerni

(10) Patent No.: US 6,709,311 B2
(45) Date of Patent: Mar. 23, 2004

(54) SPECTROSCOPIC MEASUREMENT OF THE CHEMICAL CONSTITUENTS OF A CMP SLURRY

(75) Inventor: Todd A. Cerni, Mead, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 238 days.

(21) Appl. No.: 09/928,948

(22) Filed: Aug. 13, 2001

(65) Prior Publication Data

US 2003/0032366 A1 Feb. 13, 2003

(51) Int. Cl.[7] .............................. B24B 1/00; B24B 49/00; B24B 51/00
(52) U.S. Cl. ..................... 451/5; 451/6; 451/8; 451/41; 451/36
(58) Field of Search ....................... 340/680; 356/503; 451/5, 6, 8, 41, 59, 63, 36

(56) References Cited

U.S. PATENT DOCUMENTS

| 2,741,703 | A | * | 4/1956 | Munday | ..................... 250/345 |
| 3,569,696 | A | * | 3/1971 | Karlson | ..................... 250/341.1 |
| 3,851,176 | A | * | 11/1974 | Jeunehomme et al. | ...... 250/343 |
| 3,968,367 | A | * | 7/1976 | Berg | ...................... 250/339.13 |
| 4,493,553 | A | * | 1/1985 | Korb et al. | ..................... 356/43 |
| 4,874,572 | A | | 10/1989 | Nelson et al. | |
| 5,998,215 | A | * | 12/1999 | Prather et al. | ............... 436/173 |
| 5,999,250 | A | * | 12/1999 | Hairston et al. | ............... 356/73 |
| 6,267,641 | B1 | | 7/2001 | Vanell et al. | |

FOREIGN PATENT DOCUMENTS

WO    WO 99/56106 A1    11/1999

OTHER PUBLICATIONS

Misra et al., "A Robust On–Line Technique for Determination of Oxidizer Concentration in CMP Slurries," Photonics Handbook, 4th ed., Laurin Publishing, ( Nov. 13, 1998).

Twomey, "Comparison of constrained linear inversion and an iterative nonlinear algorithm applied to the indirect estimation of particle size distributions," J. Comp. Phys., vol. 18 ( No. 2), pp. 188–200, ( Nov. 13, 1975).

Todd A. Cerni, "Aircraft–based remote sensing or tropospheric profiles for meoscale studies," Advances in Remote Sensing Retrievals, A. Deepak Publishers (Hampton, VA), pp. 339–347, ( Nov. 13, 1985).

Chahine, "Inverse problems in radiative transfer: Determination of atmospheric parameters," J. Atmos. Science, pp. 960–967, ( Nov. 13, 1970).

K.N. Liou, "An Introduction to Atmospheric Radiation," Academic Press, pp. 236–239, ( Nov. 13, 1980).

Paltridge et al., "Radiative Processes in Meteorology and Climatology," Elsevier Scientific Publishing, pp. 215–221, ( Nov. 13, 1976).

F. Scheid, "Theory and Problems of Numerical Analysis," McGraw–Hill, pp. 310–333, ( Nov. 13, 1968).

\* cited by examiner

*Primary Examiner*—Timothy V. Eley
(74) *Attorney, Agent, or Firm*—Patton Boggs LLP

(57) ABSTRACT

An apparatus and method for determining the chemical content of a chemical mechanical planarization (CMP) slurry. A CMP sample cell has windows for passing electromagnetic radiation. Three wavelengths of electromagnetic radiation, one of which is strongly absorbed by said CMP slurry and the other two of which are weakly absorbed by said CMP slurry, are directed through said sample cell to a detector, which processes a signal. A processor utilizes the signal to determine the transmission at each wavelength, then utilizes Beer's law to determine a transmission function for each wavelength, and calculates the wavelength dependent particle transmission for each wavelength using an optical model, to form a system of three equations in three unknowns, which are solved to determine a parameter representative of the chemical content of the CMP slurry.

27 Claims, 6 Drawing Sheets

SPECTROSCOPIC MEASUREMENT OF THE CHEMICAL CONSTITUENTS OF A CMP SLURRY

BACKGROUND OF THE INVENTION

1. Field of the Invention

The invention pertains to the field of chemical analysis of chemical mechanical planarization ("CMP") slurries. More specifically, it relates to an optical method of determining the chemical constituents of a CMP slurry.

2. Statement of the Problem

Integrated circuits are manufactured by depositing layers of various materials and then patterning the layers using mask and etch processes. After patterning, the incomplete integrated circuit surface usually is irregular, having steps, wells, and other structures. When a fresh layer of material is deposited over this irregular structure, the deposition generally follows the irregularities, resulting in an irregular surface for the fresh layer. Usually this is undesirable, and it is necessary to smooth the surface. CMP processes are used to planarize and smooth such surfaces. CMP has emerged as the preferred method of planarization for manufacture of multiple layer semiconductor wafers having feature sizes less than or equal to 0.35 microns. CMP is also used in the optics industry for similar purposes.

CMP process slurries typically consist of a high concentration of sub-micron size abrasive particles, such as $SiO_2$, $Al_2O_3$ or $CeO_2$ particles, suspended in a chemically active agent, such as an acid or base solution. The abrasive concentration is generally 4% to 18% solids by weight. $SiO_2$ slurries are referred to in the art as "oxide" slurries, and $Al_2O_3$ slurries are referred to as "metal" slurries. CMP slurry manufacturers attempt to produce slurries that consist predominantly of particles less than 1.0 or even 0.5 microns in size.

Since CMP slurries intimately contact the materials out of which the integrated circuit or optics components are made, it is important that the chemical content of the slurry be known and controlled. For example, materials that are planarized and chemicals used in other integrated circuit manufacturing processes can get into the slurry and affect subsequent layers when they are planarized. Further, the chemicals and materials that make up the slurry can decompose over time. Therefore, it is important to be able to periodically check the chemical composition of a CMP slurry. In the past, this has been done by analytical chemical means, such as titration. However, such methods are slow, consume expensive chemicals, and create a hazardous chemical waste stream. Automated titration systems may require thirty minutes to make a measurement, whereas optical methods typically require only one to ten seconds.

Recently, it has been suggested that an optical device can be used to determine some chemicals in a CMP slurry. See U.S. Pat. No. 6,267,641 B1 issued Jul. 31, 2001 to J. F. Vanell and C. B. Bray. This patent describe a means of measuring the hydrogen peroxide content of CMP slurries, by inserting a commercially available refractometer into a sample chamber containing the slurry. However, a refractometer relies on an index of refractive difference between hydrogen peroxide and water, and is not very sensitive, due to the substantially opaque nature of the slurry. The minimum detectable concentration of hydrogen peroxide, using a refractometer, is on the order of 0.5%. See A. Misra and M. L. Fisher: "A Robust On-Line Technique for Determination of Oxidizer Concentration in CMP Slurries", *SEMICON West* 2001, *Symposium Proceedings for Innovations in Semiconductor Manufacturing*; and *Photonics Handbook*, Book 4, 44th Edition, 1998, Laurin Publishing. Those CMP slurries which utilize hydrogen peroxide as the active chemical have a concentration of 2%–5% hydrogen peroxide by weight. For these relatively high concentrations of active chemicals, refractometers yield an adequate solution. However, for other chemicals, much more sensitivity is required. For example, organic liquids may be used as the chemically active agent, in concentrations down to 200 ppmV (0.02%), far below the detectable limit exhibited by refractometers for measurement of hydrogen peroxide. Furthermore, refractive index measurements are very temperature sensitive, and require tight control of the sample temperature to obtain accurate results.

Thus, there remains a need for a real-time probe to enable determination of the chemical content of a CMP slurry that does not require removal and analysis of a portion of the CMP slurry.

It is, accordingly, one object of the invention to provide a probe and/or system which provides real-time measurement of CMP slurry particle size distributions and/or change of the particle size distribution. Another object of the invention is to provide a quality control process to detect acceptable and unacceptable CMP slurries, real-time, in a manufacturing environment. Yet another object of the invention is to provide systems and methods for detecting CMP slurry particle size distributions and/or changes in such distributions. These and other objects of the invention are apparent within the description which follows.

SUMMARY OF THE INVENTION

The present invention overcomes the problems outlined above, and advances the art, by providing real-time systems, methods and/or probes for continuous chemical analysis of undiluted CMP slurry. The CMP slurry can include a broad range of chemicals. The systems and methods of the invention provide high sensitivity to small changes in the chemical characteristics of the CMP slurry, and preferably with autonomous operation in an industrial environment. These advantages are obtained, in certain aspects, by measuring spectral transmission through undiluted CMP slurry samples (typically through a slurry "flow"). The spectral transmission measurements are made at one or more wavelengths, and preferably at three or more wavelengths. In particular, the preferred system of the invention provides an apparatus and a method for accurately determining the concentration of active chemicals in CMP slurry, through on-line, continuous sampling of undiluted slurry, using spectroscopic means.

In one aspect, a probe according to the invention measures the concentration of active chemical species in CMP slurry with undiluted, continuous, on-line sampling for real-time process control, the probe preferably including a plurality of light sources, a detector system which includes one or more fixed grating linear detector array spectrometers and sample cells, a three-position chopper, and an optical pathway for transmitting light from the light sources through the sample cells and then to the detector system or spectrometers. A computer or microprocessor receives detector signals and performs calculations to determine the concentration of chemical species. The sample cells are specially constructed to reduce optical depth in the slurry, which permits chemical concentration measurements without dilution of the slurry.

In another aspect, the invention preferably determines a slope of transmission as a function of the wavelengths. This determination of a change in the slope is preferably made "over time" such that a change in slope indicates a change in the chemical content of the slurry. Further, the slope is preferably determined logarithmically. That is, the process preferably includes the step of determining a logarithmic slope of transmission as a function of the wavelengths.

In another aspect, the invention provides a method and apparatus for determining a change in the logarithmic slope over time. The change in logarithmic slope indicates a change in chemical concentration.

In one aspect of the invention, radiation wavelengths selected for transmission through the CMP slurry are isolated by a grating or other dispersive optical element (e.g., a prism). The wavelengths can alternatively be determined by using a laser with a known wavelength emission. In a preferred aspect, wavelength selection is made through use of one or more bandpass filters (and preferably three filters), such as within a filter wheel. A combination of the above spectral discriminators can also be used, as needed, in accord with the invention. An order sorting filter is optionally included with any of these dispersive discriminators.

In yet another aspect, the invention provides a method and apparatus that compares the transmission to a reference transmission indicative of a preferred chemical content within a flow of the CMP slurry. Preferably, a method and apparatus for storing the reference transmission in memory is provided and a comparison between the reference transmission and the actual transmission is made electronically and in real time.

Alternatively, the invention provides a method of (a) storing a plurality of reference transmissions, where each reference transmission corresponds to a particular CMP slurry flow and chemical content, and (b) selecting one reference transmission and comparing the transmission to the selected reference transmission.

A process of the invention can further include comparing transmission information with an empirical curve of extinction efficiency versus particle size diameter to determine chemical content of the slurry.

The invention also provides a system for evaluating CMP slurry quality in a process. In this aspect, a light source generates a beam of electromagnetic radiation for transmission through a flow of the slurry. A spectral discriminator isolates at least two, and preferably three, wavelength bands of the radiation prior to transmission of the radiation through the flow. A detector detects radiation transmitted through the flow. A processor evaluates transmission of the wavelength bands through the flow to determine chemical changes in the CMP slurry.

In one aspect, a computer with a processor serves as the processor of the system, to process signals and to make determinations and calculations. Those skilled in the art should appreciate that other processors, e.g., an ASIC, can alternatively be used.

In yet another aspect, a system of the invention includes memory, coupled to the processor, to store one or more reference transmissions. Each of the reference transmissions corresponds to a particular CMP slurry flow and chemical make up. The processor selects one reference transmission and compares the transmission through the flow to the selected reference transmission to detect changes in the particle size distribution. The memory can further store other reference data for comparison to other changes in chemical characteristics of the CMP slurry, in accord with the invention.

In still another aspect, the memory of the invention can store data indicative of extinction efficiency as a function of chemical content. The processor then compares the transmission to the data to determine chemical content of the slurry.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which:

FIG. 6 schematically illustrates a process flow of the invention for detecting and informing users of unacceptable CMP slurry chemical compositions, in near real-time; and

DETAILED DESCRIPTION OF THE PREFERRED EMBODIMENT

Figure 1:
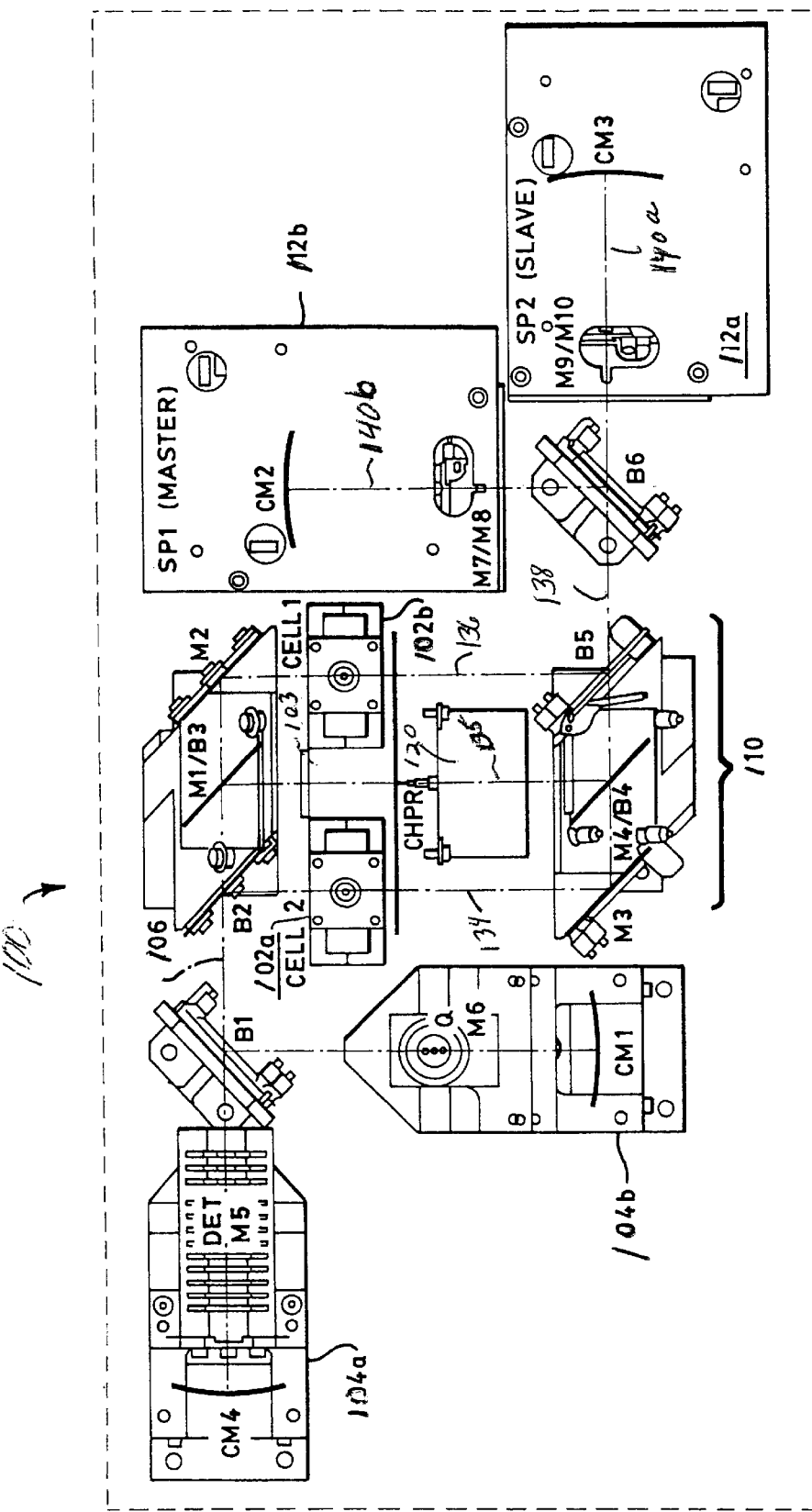
FIG. 1 schematically shows a preferred CMP slurry chemical measuring system constructed according to the invention.

FIG. 1 depicts a schematic of a preferred embodiment of a CMP slurry chemical content measuring and quality control system 100 constructed according to the invention. System 100 includes radiation sources 104a and 104b, sample cells 102a and 102b, and detectors 112a and 112b, as well as optics, such as 110, for directing the radiation from the sources, through the sample cells, to the detectors. The sample cells 102a, 102b, which will be described in detail below, are designed to extend the spectral range within which one obtains high accuracy transmission measurements to determine CMP slurry chemical content. Source 104a includes a deuterium lamp (DET) and a mirror M5 which directs the light from the deuterium lamp to curved mirror CM4, which collimates the radiation and directs it to beam-splitter 108. Source 104b includes a quartz/tungsten halogen lamp (Q) and a mirror M6 which directs the light from the deuterium lamp to curved mirror CM1, which collimates the radiation and directs it to beam-splitter B1. Thus, sources 104a and 104b generate radiation in different wavebands which are combined into beam 106 via beam-splitter B1. Beam-splitter B2 directs a portion 134 of the beam 106 through sample cell 102a, and mirror M2 directs another portion 136 through sample cell 102b. Mirrors M1, M2 and beam-splitters B2 and B3 comprise a fixed quad optics block, which is used to direct the radiation through the sample cells and an empty region or hole 103 which is used for calibration. Mirrors M3 and M4 and beam-splitters B4 and B5 comprise an adjustable quad optics block which is used to recombine the beams into one after they have passed through the sample cells 102a and 102b and the hole 103. Chopper 120 interrupts the beam through the hole 103 by stepping to one position, followed by a measurement, then to another position, followed by a measurement, and with steps performed about every ten seconds. Mirror M1 directs a portion of beam 106 upward and beam-splitter B3 then directs it across to hole 203 and chopper 120, while beam-splitter B4 and mirror M4 reverses these directions so that the beam 135 rejoins beams 134 and 136 to form recombined beam 138. Beam-splitter B6 sends a portion 140a of beam 138 to detector 112a and another portion 140b to detector 112b. In detector 112a, the beam 140a first strikes curved mirror CM3, which directs the beam to flat mirrors M9/M10 which directs it to a grating and thence to a 2048 element CCD (charge coupled detector). Similarly, in detector 112b, the beam 140b first strikes curved mirror CM2, which directs the beam to flat mirrors M7/M8 which directs it to a grating and thence to a 2048 element CCD (charge coupled detector). The detectors 112a and 112b are miniature fixed grating linear detector array spectrometer modules model S2000 made by Ocean Optics. The entire CMP slurry chemical measuring system 100 has a footprint of about 12.5 inches by 26.5 inches.

While, for ease of understanding, the system 100 has been described in terms of two different light sources, in the preferred embodiment three or more sources may be used, as discussed below with respect to FIG. 4.

Figure 2:
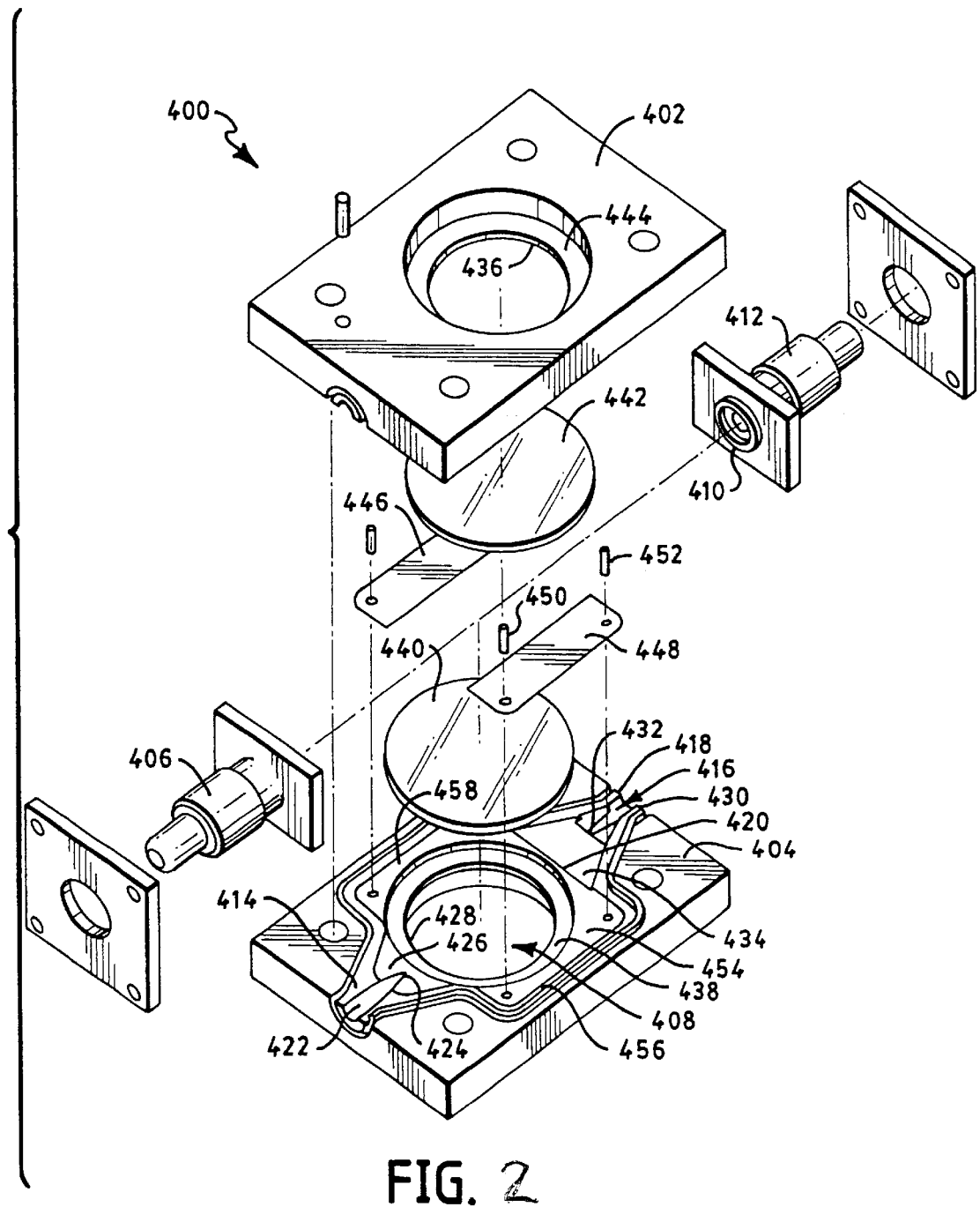
FIG. 2 depicts, in an exploded view, a first specially constructed sample cell for use in the probe of FIG. 1.

FIG. 2 depicts a preferred volumetric sample cell 400 for use the spectrometer system of FIG. 1. A housing is formed of top plate 402 and bottom plate 404, which are each machined from a solid, slightly deformable block of chemically resistant material such as TFE Teflon. Sample cell inlet line 406 is connected with an inlet port (not depicted) through which undiluted CMP slurry from the main CMP slurry line enters the interior space 408 of sample cell 400. Outlet port 410 drains the slurry from space 408 into outlet line 412. Each of top plate 402 and bottom plate 404 are provided with an opposed pair of triangular tapered ramps, e.g., ramps 414 and 416. These ramps are thickest at their respective tips proximate the corresponding port, e.g., tip 418 proximate outlet port 416, and which widen and narrow towards a base remote from the port, e.g., base 420. Ramp 414 contains a conical opening having a maximum volume proximate cell inlet line 406. This volume decreases towards ramp 416 with decreasing volume in the conical opening 422 being equally compensated by increased volume in the portion of ramp 414 surrounding conical opening 422. Conical opening 422 terminates at tip 424 proximate a wedge 426 of increasing narrow width and steepness leading to an interior opening 428. Ramp 416 has a similar conical opening 430 with tip 432 pointing towards ramp 414 and terminating prior to wedge 434.

Each of top and bottom plates 402 and 404 are respectively provided with centrally located circular apertures 428 and 436, which are slightly offset along the fluid flow axis. The interior portions of plates 402 and 404 each contain a first step surrounding the corresponding opening, e.g., first step 438 surrounding opening 428, for receipt of a corresponding sapphire window. For example, a flat sapphire window 440 is received in sealing engagement against step 438. Flat sapphire window 442 identical to window 440 is similarly received in sealing engagement against step 444. A pair of opposed spacers 446 and 448 are retained against flow by corresponding retaining pins, e.g., retaining pins 450 and 452, and fit between the sapphire windows 440 and 442. Each spacer is retained within the confines of a correspondingly sized recess, e.g., as spacer 448 is retained within recess 454. A deformable elastomeric wall 456 sealingly engages top plate 402 and bottom plate 404 to prevent leakage from sample cell 400. Wedges 426 and 434 extend wide enough to meet the spacers 448 and 446. Spacers 446, 448 each sealingly engage both windows 440 and 442. Thus, there is no slurry leakage from the space between windows 440 and 442, i.e., cell 400 is a volumetric cell because it does not leak into space 458 circumscribing windows 440 and 442. That is, all or at least a high percentage of the slurry that passes through the system is monitored. The optical viewing area between windows 440 and 442 preferably ranges between 50 and 250 microns (and up to about 2000 microns in certain embodiments) in thickness for use with optically dense slurries.

Sample cell 400 operates as follows. The sapphire windows 440 and 442 together with opposed spacers 446 and 448 define the optical viewing area available to path 134 or 136 (see FIG. 1). The slurry fills the space between the two sapphire windows, and the transmission path length through sample cell 400 equals the thickness of spacers 446 and 448. The tapered ramps 414 and 416 are carefully machined into the corresponding plates 402 and 404 to provide a smooth transition between the input/output lines 406 and 412 relative to the optical viewing area between windows 440 and 442. This smooth transition prevents slurry agglomeration.

Measurement of light scattering as a function of angle is also a sensitive measurement technique for CMP slurry chemical analysis. A major disadvantage of this approach is that significant multiple scattering errors appear when the optical depth exceeds 0.1–0.2. Optical depth is the dimensionless extinction parameter in the exponential transmission function of Beer's law, known in the art, and is defined as the product of an extinction per unit length in the slurry times a thickness of the slurry in an optical path through the sample cell. Optically dense slurry is hereby defined as a particulate poly-dispersion consisting of 1%–30% solids by weight of sub-micron particles suspended in a liquid. CMP slurries are optically dense slurries that typically exhibit an optical depth of greater than 10, at 0.5 microns wavelength in a conventional sample cell having a one centimeter path length, yielding a transmission of less than 0.00005. This measurement technique relies upon an unambiguous definition of the scattering angle for each photon. For a doubly scattered photon, the scattering angle for each scattering event is undefined. This limitation necessitates a batch sampling mode of operation, with large amounts of dilution.

By comparison, the spectral transmission measurement technique can operate at optical depths as large as approximately 3.0, allowing one to sample undiluted slurry in a continuous, real-time mode, with realistic sample cell dimensions. The spectral transmission measurement technique does not suffer from multiple scattering errors until the diffuse radiation field intercepted by the sensor's narrow field of view (typically about 1°), becomes a significant percentage of that remaining in the direct beam.

The slurry chemical makeup is retrieved from the spectral transmission measurements through utilization of a modified Twomey/Chahine nonlinear inversion algorithm. Equation (1) expresses the measured transmission (T) as a function of wavelength ($\lambda$) in terms of the transmission of sample cell windows ($T_W$), the transmission of the liquid portion of the slurry ($T_L$), and the transmission of the slurry particles ($T_P$).

$$T(\lambda)=T_W(\lambda)T_L(\lambda)T_P(\lambda) \quad (1)$$

By first measuring the transmission of the sample cell filled only with the liquid portion of the slurry, then dividing that into the transmission expressed in Equation (1), one can isolate $T_P(\lambda)$, which is the quantity of interest. Beer's Law is then solved for the particle volume extinction coefficient ($\beta_E(\lambda)$), as shown in Equation (2), where L is the transmission path length or sample cell width. Equation (3) represents the formula for calculating the particle volume extinction coefficient in terms of the particle radius (r), the Mie extinction efficiency ($Q_E$), and the PSD (N(r)), where m is the particle's complex refractive index.

$$\beta_E(\lambda) = -ln(T_P(\lambda))/L \quad (2)$$

$$\beta_E(\lambda) = \pi r^2 Q_E(2\pi r/\lambda, m) N(r) dr \quad (3)$$

Equation (3) is inverted to solve for the particle size distribution. One class of inversion algorithms is the linear inversion, which provides a less preferred model for reasons that are explained below. The less preferred inversion method transforms the measurement equation into a linear system of equations by replacing the integral with a summation and by representing the collection of equations in the matrix form given by Equation (4). In this latter equation, elements of matrix $Q$ consist of $\pi r^2 Q_E$. The $Q$ matrix has m rows, one for each wavelength, and n columns, one for each radius; m must be greater than or equal to n. The $\underline{N}$ matrix is n by 1, and the elements consist of the particle size distribution. The $\underline{\beta}$ matrix is m by 1, and the elements consist of the measured spectral volume extinction coefficients.

$$\underline{Q}_{\lambda,R} \underline{N}_R = \underline{\beta}_\lambda \quad (4)$$

Equation (4) can be formally inverted to solve for the particle size distribution, utilizing conventional inversion algorithms which constrain the solution to various conditions, such as smoothing (minimize the first or second derivative), or minimize the departure from a first guess, according to Twomey, *Comparison of constrained linear inversion and an iterative nonlinear algorithm applied to the indirect estimation of particle size distributions*, J. Comp. Phys., Vol. 18, No. 2, pp. 188–200 (1975), which is hereby incorporated by reference to the same extent as though fully disclosed herein.

Constraints are required in all inversion algorithms because the existence of measurement error and quadrature error (replacing the integral with a sum) result in the fact that a family of particle size distributions will satisfy the measurement equation. For any inversion method, the uncertainty in the retrieved solution can be reduced by: (a) choosing a more sensitive measurement technique; (b) reducing the measurement error; or (c) increasing the number of measurements, which reduces the effects of quadrature error.

Linear inversion techniques are computationally efficient, but they are a poor choice for the CMP slurry problem because the most popular constraint, i.e., that of smoothing, is a poor choice for slurry analysis. The chemical content of a slurry may not be smooth or continuous. Additionally, linear inversion algorithms can be unstable to an extent that produces physically unrealistic answers.

The CMP slurry measurement problem consists of detecting departures from the normal or specified chemical content, which makes a non-linear, iterative, inversion algorithm a natural choice and a more preferred model for use in practicing the invention. With the iterative approach, one can start with the normal chemical content as a first guess. The iterative calculations converge toward a final solution in an orderly fashion, where convergence is based upon a difference between the measured spectral extinction and that calculated from the last guess particle size distribution. Alternatively, one can start with a delta function as a first guess. Iteration is halted when this difference becomes less than some predetermined error bound. This preferred method of inverting equation (4) is based on previous work in the field of atmospheric remote sensing by Cerni, "Aircraft-based remote sensing or tropospheric profiles for meoscale studies", *Advances in Remote Sensing Retrievals*, pp. 339–347, A. Deepak Publ., Hampton, Va. (1985); and Chahine, "Inverse problems in radiative transfer: Determination of atmospheric parameters", *J. Atmos. Sci.*, Vol. 27, pp 960–967 (1970) and Twomey (1975, referenced earlier), which are incorporated by reference herein to the same extent as though fully disclosed herein.

The algorithm given in Equations (5) and (6) is a preferred means of inverting the spectral transmission data to retrieve the particle size distribution. The superscripts I and I–1 refer to successive numbers of iterations. The subscripts P refer to different wavelengths, and indicate that all the measurements are utilized in adjusting the chemical content particle size distribution at a single r value. Additionally, one can improve the accuracy of the retrieval by adding conservation of mass (slurry percent solids by weight), and summing Equation (5) over all wavelengths.

$$N_P^{(I)}(r) = [1 + (r_P^{(I-1)} - 1)\pi r^2 Q_E(2\pi r/\lambda, m)] N_P^{(I-1)}(r) \quad (5)$$

$$r_P^{(I-1)} = \beta_E(\lambda)/[\int \pi r^2 Q_E(2\pi r/\lambda, m) N_P^{(I-1)}(r) dr] \quad (6)$$

Figure 3:
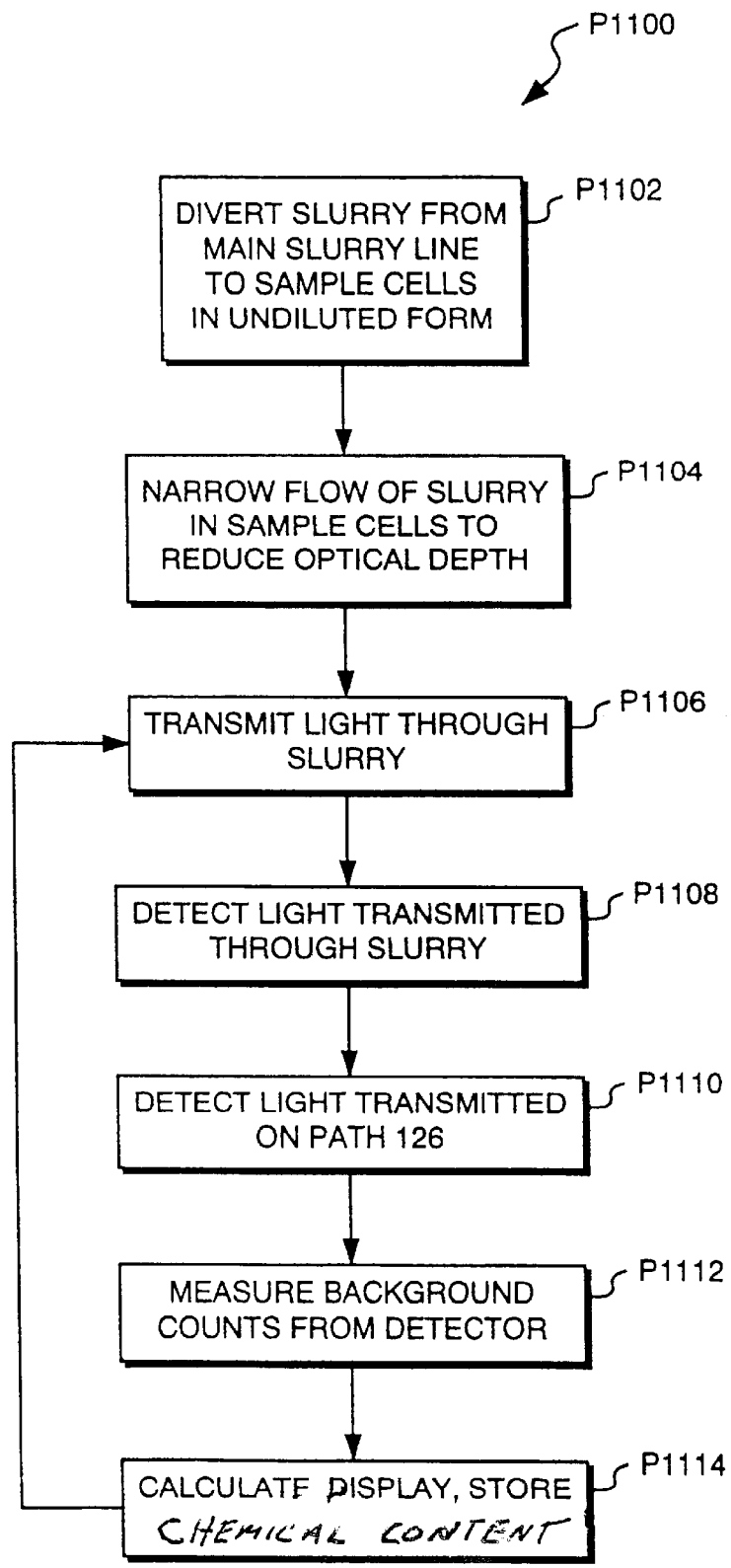
FIG. 3 depicts a schematic process diagram for use in operating the probe shown in FIG. 1.

FIG. 3 depicts a schematic process diagram of process P1100 for use in operating the probe shown in FIG. 1. In step P1102, optically dense CMP slurry is diverted from the main slurry line to the sample cells 102a and 102b. In step P1104, the flow of slurry is narrowed through the sample cells to provide an optical depth that permits meaningful spectral transmission data. Light is transmitted through the narrowed slurry along pathways 134 and 136 in step P1106. Pathways 140a and 140b deliver this light to the spectrophotometers 112a and 112b in step P1108. The spectrophotometers produce signals representative of the detected light and chemicals in the cells 102a and 102b. These signals are transmitted to CPU 1220 (FIG. 4) for processing according to the modified Twomey/Chahine technique according to equations 1–6.

At the conclusion of step P1108, step P1110 includes the detection of light transmitted along pathway 135 to spectrophotometers 112a and 112b due to the rotation of chopper blade 130 and the reflective action of mirrors M1, M4 and the actions of beam splitters B2 and B4. The detector counts are transmitted to CPU 1220 for registration of source lighting conditions without slurry absorption in sample cells 102a and 102b.

In step P1112, the detector background count is measured with chopper blade 120 positioned to place a solid disk in path 135 for blocking the transmission of light. Spectrophotometers 112a and 112b again produce signals corresponding to detected light, and these signals are transmitted to CPU 1220, which interprets the signals as background count information that can be subtracted from total counts received from light traveling along pathways 134 or 136.

In step P1114, CPU 1220 uses stored detector signals from steps P1108, P1110, and P1112 to calculate, display and store a particular chemical content, as discussed above. Steps P1106–1114 are continuously repeated to perform real-time measurements of the chemical content in the CMP slurry.

Figure 4:
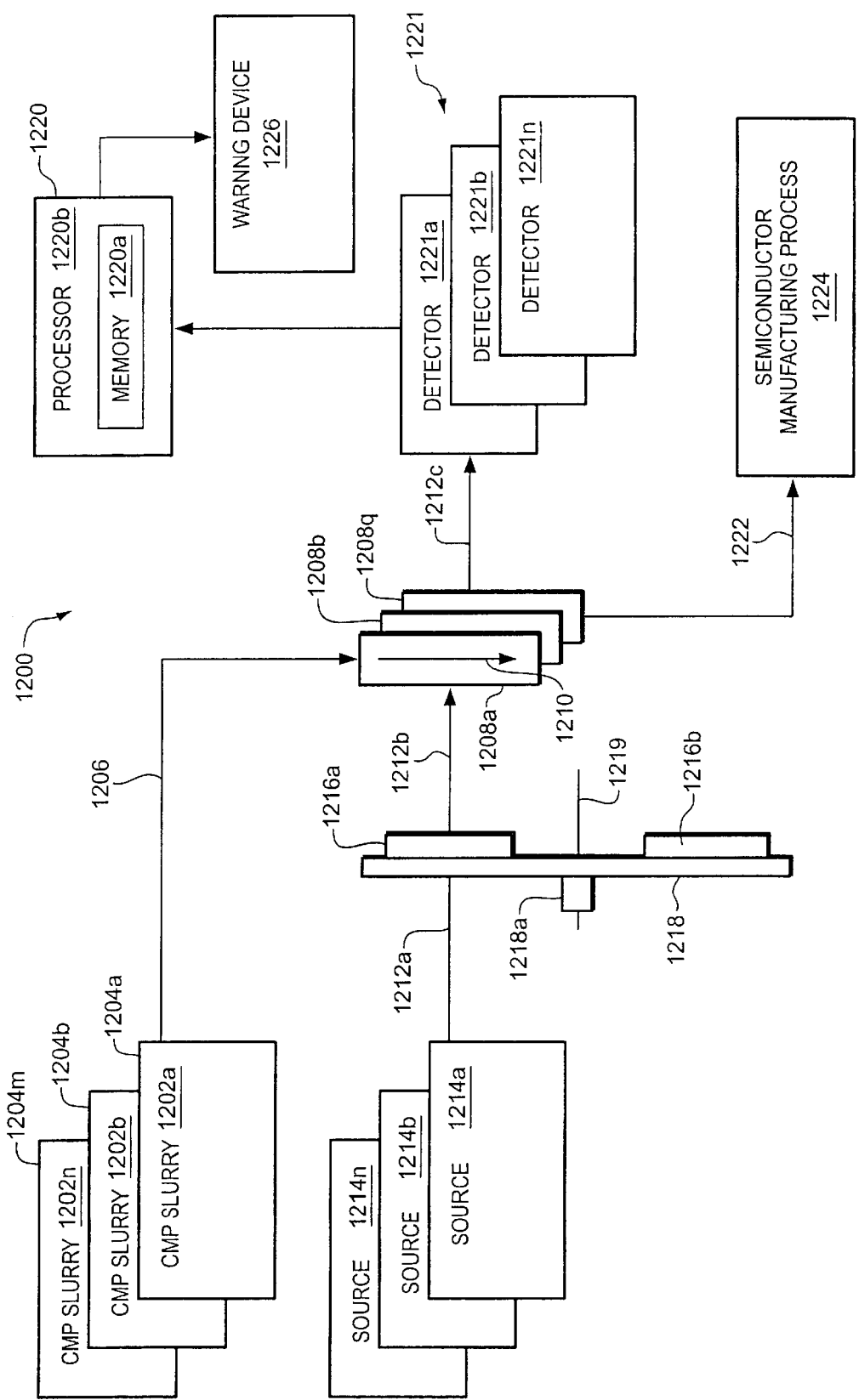
FIG. 4 illustrates the preferred embodiment of a CMP slurry analysis system constructed according to the invention.

FIG. 4 shows a preferred embodiment of CMP slurry chemical quality control system 1200 constructed according to the invention. CMP slurry 1202 from CMP slurry supply 1204 is transmitted through supply line 1206 to a sample cell 1208, e.g., sample cell 400 of FIG. 2. Sample cell 1208 provides for efficient and uniform CMP slurry flow 1210 through cell 1208 so that radiation 1212 may be transmitted therethrough, as discussed in FIG. 1 above in connection with beams 134, 136.

Source 1214 generates radiation 1212. By way of example, source 1214 can be a quartz tungsten halogen source, generating infrared and/or visible radiation 1212, or a deuterium source, generating ultraviolet radiation. Preferably, source 1214 is "broadband" so as to provide multiple wavelength bands which generate radiation 1212. However, multiple sources 1214a, 1214b . . . 1214n can be used, selectively, to generate desired radiation wavelengths 1212a, as required. For example, to generate ultraviolet light, source 1214b can represent a deuterium source; while to generate infrared or visible light wavelengths, source 1214a can represent a tungsten lamp. To switch between sources 1214, an beam splitter/chopper arrangement similar to those shown in FIG. 1 can be used, or alternative techniques can be used to accomplish the same function, such as through mechanical actuation.

In the preferred embodiment, filters 1216 spectrally discriminate source radiation wavelengths 1212a emitted from source 1214 such that only selected wavelengths 1214b pass through filters 1216. Multiple filters 1216a, 1216b can be used to alternatively pass and select different wavebands to illuminate sample 1208. By way of example, filters 1216 are shown arranged on filter wheel 1218 which is rotated about axis 1219 by motor controller 1218a, selectively, to alternatively position filters 1216a, 1216b in the path of radiation 1212a. Filter wheel 1218, controller 1218a, and filters 1216 are known to those skilled in the art of optics. In this manner, radiation 1212b of desired waveband can be selected by a user of system 1200. Filters 1216 are moved to block radiation 1212a as needed to select the appropriate wavelength band as emitted from source(s) 1214.

Although two filters 1216 are shown, those skilled in the art should appreciate that one or more filters can be used in system 1200 to achieve the objectives herein. In the preferred embodiment, three filters are used.

Radiation 1212c transmitted through sample cell 1208 corresponds to radiation also transmitted through CMP slurry flow 1210. A detector 1221 detects radiation 1212c and generates signals indicative of transmission of radiation 1212b through sample and flow 1208, 1210. These signals are interpreted by processor 1220, e.g., a computer, to determine a transmission value as a function of wavelength (or waveband). By way of example, if source 1214 generates radiation 1212a that is filtered by filter 1216a to 2.5 microns +/−0.2 microns, then detector 1220a can correspond to a near infrared detector, e.g., InGaAs, to detect transmission of radiation 1212c through sample and flow 1208, 1210. Transmission is determined by computer 1220 and associated with "2.5 microns."

At times, multiple detectors 1221a, 1221b . . . 1221n are required to detect all the wavelengths of interest from sources 1214a, 1214b . . . 1214n. Detectors 1221 can be inserted within system 1200, as needed, to measure appropriate wavelengths, or an appropriate optical technique such as illustrated in FIG. 1 can be used to achieve the same function.

The most preferred embodiment of the invention utilizes a spectrometer as described in reference to FIGS. 1 and 4 to measure differential absorption. Differential absorption relies on measurement of the transmission through a sample at two closely spaced wavelengths, one of which is strongly absorbed and the other of which is weakly absorbed or not absorbed. Here, "closely spaced" means that the two wavelengths are within a distance less than or equal to the $1/e^2$ width of an average absorption band of the CMP slurry; generally the wavelengths are selected so that they are on the same steep slope of the same chemical absorption band, with one high up on the slope, and therefor strongly absorbed, and the other well down on the slope so that it is weakly absorbed. "Strongly absorbed" and "weakly absorbed" are relative terms defined by the requirement that ln(T strong)/ln(T weak) 3, where T is the transmissivity. Note that the log natural of a transmissivity will generally be a negative number, and when this ratio is formed, the negative signs cancel. Thus, although the transmissivity is a smaller number, in that it is a larger negative number for a strongly absorbed wavelength, the described ration will generally be a number greater than one. Further the sample cell optical path length cancels out when the ratio of extinction coefficients is formed, provided that both transmission measurements are made with the same sample cell. The ratio of transmissions at these two wavelengths is related to the concentration of the chemical species of interest, through the use of Beer's law or other suitable transmission function. See U.S. Pat. No. 4,874,572 issued Oct. 17, 1989, to L. Nelson, and T. A. Cerni, which is hereby incorporated by reference as though fully disclosed herein. If the two wavelengths are closely spaced, most instrument response variations with time and temperature automatically cancel, making differential absorption a very powerful measurement technique. This nullification of instrument response variations requires an optical system design as discussed herein to be fully realized.

The challenge for implementation of differential absorption methods with CMP slurry is that the slurry particles perturb the measurement by imposing a wavelength dependant transmission of their own. The spectral signature of the particle transmission is superimposed on the spectral absorption signature of the liquid one is attempting to measure. The transmission at any given wavelength, due to the slurry particles alone, depends on their concentration and size distribution, which in general is unknown. Furthermore, in the UV portion of the spectrum, where hydrogen peroxide absorbs, the slurry may be totally opaque over path lengths as short as 0.1 mm, due to particle extinction, making transmission measurements impractical.

Implementation of the differential absorption measurement technique for CMP slurry most preferably includes measurement of the slurry transmission at three or more wavelengths, one of which is strongly absorbed by the liquid chemical species of interest, while the remaining wavelengths are weakly or not absorbed by the chemical species. Data analysis consists of modeling the particle transmission with a wavelength dependent function, then modeling the liquid absorption with Beer's law or other suitable transmission function. If the spectral bandwidth of a particular wavelength measurement is small, then Beers law yields an accurate prediction of the liquid absorption as a function of chemical species concentration. However, if the spectral bandwidth of a measurement is large, relative to the width of the absorption band, other more complex transmission functions may be required to predict transmission as a function of chemical concentration. See the Nelson and Cerni patent referenced above. The optical model for wavelength dependent particle transmission is then combined with the transmission function for the absorbing chemical species to form three or more simultaneous equations, with the number of equations equal to the number of wavelengths at which transmission measurements are made. This series of simultaneous equations is then solved to obtain the concentration of the liquid chemical species of interest.

The preferred number of wavelengths is three or more. A larger number of wavelengths allows for a more complicated optical model for particle transmission. The following derivation demonstrates implementation of the analysis method for the case of three wavelengths and utilization of Beer's law for the liquid chemical transmission function. The optical model chosen here for particle transmission, which is described in Equation 8 below, is described in Liou, K. N., *An Introduction to Atmospheric Radiation*, Academic Press, 1980; and Paltridge, G. W. and Platt, C. M. R. Platt, *Radiative Processes in Meteorology and Climatology*, Elsevier Scientific Publishing, 1976.

Using the following quantities:

T=Transmission through the slurry,

Z=Thickness of sample cell (cm), $T_P$=Transmission due to particles in slurry,

K=Liquid absorption coefficient, $T_L$=Transmission due to liquid portion of slurry, ρ=Chemical concentration, $β_P$=Extinction coefficient for particles (1/cm), C, α=Particle model coefficients, $β_L$=Extinction coefficient for liquid (1/cm), λ=wavelength one can calculate:

$$T = T_P T_L = exp(-β_P Z) exp(-β_L Z) \quad (7)$$

$$β_P = Cλ^{-α}, \text{ and} \quad (8)$$

$$β_L = Kρ \quad (9)$$

In the following, the subscripts 1, 2 and 3 refer to the three measurement wavelengths. Equations 10–12 are obtained by combining Equations 7–9.

$$T_1 = exp(-Cλ_1^{-α}Z) exp(-K_1 ρ Z) \quad (10)$$

$$T_2 = exp(-Cλ_2^{-α}Z) exp(-K_2 ρ Z) \quad (11)$$

$$T_3 = exp(-Cλ_3^{-α}Z) exp(-K_3 ρ Z) \quad (12)$$

Next, transmission ratios are formed by dividing the above equations by each other. This implements the differential absorption measurement technique, with it's inherent immunity to drift in instrument responsivity. Then the natural logarithm of each equation is taken, to eliminate the exponential functions. The result is Equations 13–15.

$$-ln(T_1/T_2) = CZ(λ_1^{-α} - λ_2^{-α}) + ρZ(K_1 - K_2) \quad (13)$$

$$-ln(T_1/T_3) = CZ(λ_1^{-α} - λ_3^{-α}) + ρZ(K_1 - K_3) \quad (14)$$

$$-ln(T_2/T_3) = CZ(λ_2^{-α} - λ_3^{-α}) + ρZ(K_2 - K_3) \quad (15)$$

Equations 13–15 constitute a set of three independent equations in three unknowns: C, α, ρ. All other parameters can be calculated or derived from calibration procedures. Therefore, one can solve this set of equations for all three unknowns; of course the primary variable of interest is ρ, the concentration of the chemically active liquid compound. Since this set of equations is highly non-linear, it cannot be solved in closed form, via ordinary algebraic means. Rather, the solution to this set of equations requires numerical methods routinely used to solve non-linear sets of equations. See Scheid, F., Theory and Problems of Numerical Analysis, McGraw-Hill, 1968.

Differential absorption is a much more sensitive and accurate means of measuring the chemical composition of a CMP slurry sample, as compared to the prior art. Differential absorption is routinely capable of chemical detection limits of significantly less than 1–10 ppmV. Organic chemicals, such as those used in CMP slurries, typically exhibit strong absorption bands, particularly in the infrared spectral region, which can be accessed by differential absorption instruments as described herein.

Returning to FIG. 4, different slurry supplies 1204a, 1204b . . . 1204m can also be coupled to system 1200 in a manufacturing process; and each CMP slurry 1202a, 1202b . . . 1202m can then be coupled to sample cell 1208 as required through appropriate flow pathways 1206. Alternative sample cells 1208a, 1208b . . . 1208q can be used in system 1200, as needed, to acquire appropriate optical path lengths corresponding to enhanced detection of radiation 1212b through sample cell and flow 1208, 1210. As before, sample cells 1208 can be switched into system 1200 manually, or mechanically, or an optical configuration such as FIG. 1 can be used to achieve the same function (i.e., multiple samples are mounted within system 1200 and radiation of the appropriate wavelength is re-routed to the correct sample cell 1208 through different optical paths and beam-splitters).

CMP slurry from flow 1210 leaves sample cell 1208 along slurry line 1222, which couples to semiconductor manufacturing process 1224. When system 1200 detects bad CMP slurry, as discussed herein (e.g., slurry with a chemical content extending beyond a desirable range), then processor 1220 sends a warning signal to warning device 1226, e.g., a light, audible alarm or other device (e.g., a computer) coupled or proximate to manufacturing process 1224. In this manner, manufacturing process 1224 is informed, in real-time, of CMP slurry chemical quality control issues which can damage and destroy semiconductor surfaces used in integrated circuit devices.

The function of source(s) 1214 and filter(s) 1216 can be replaced by laser diodes, if desired. Alternatively, filter(s) 1216 can be replaced by appropriate dispersive elements (e.g., gratings) located with detector(s) 1221, such as discussed in connection with FIG. 1.

Figure 5:
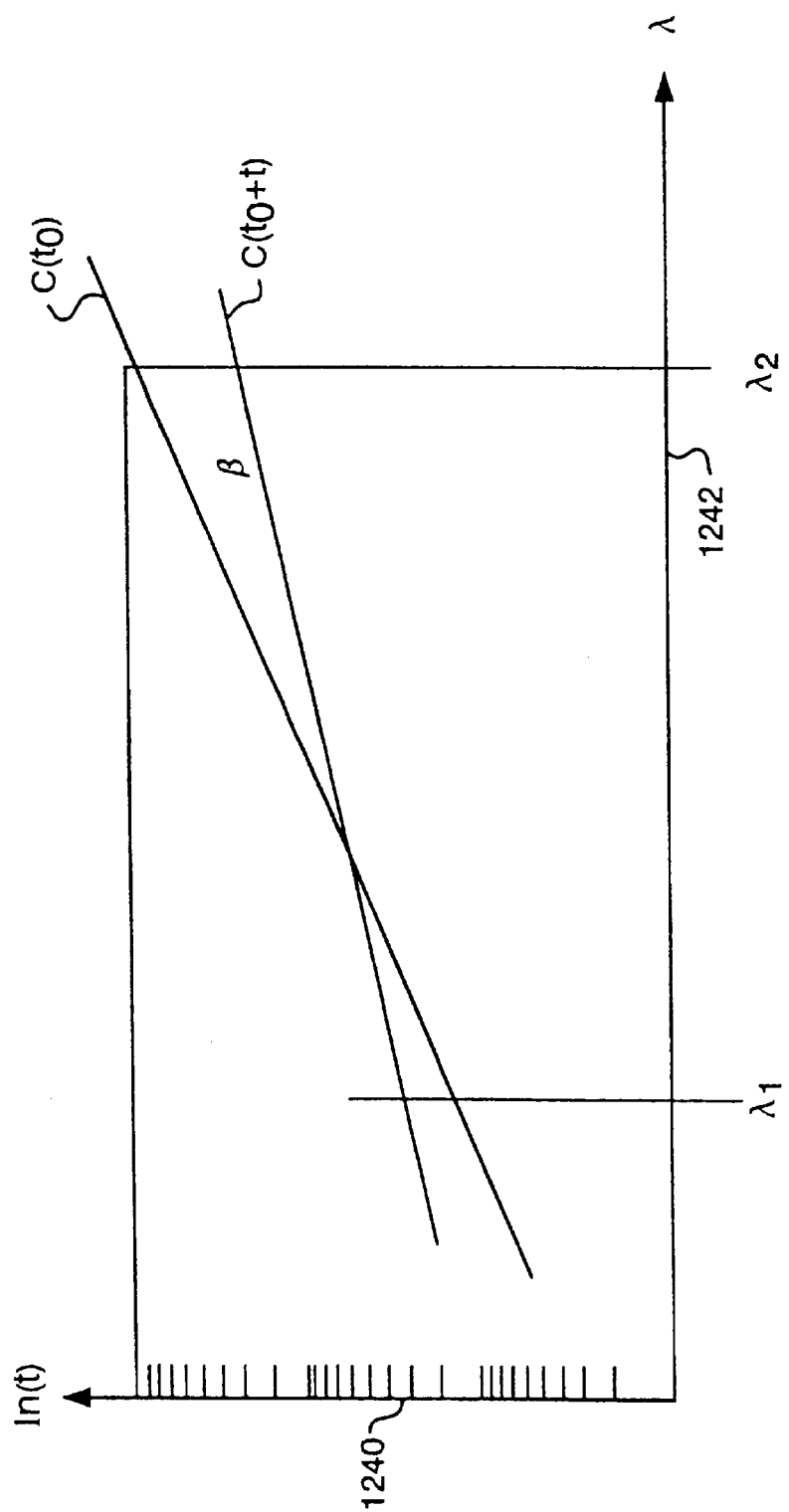
FIG. 5 illustrates representative transmission versus wavelength curves generated in accord with the invention to detect "good" versus "bad" CMP slurries during chemical analysis.
Figure 9:
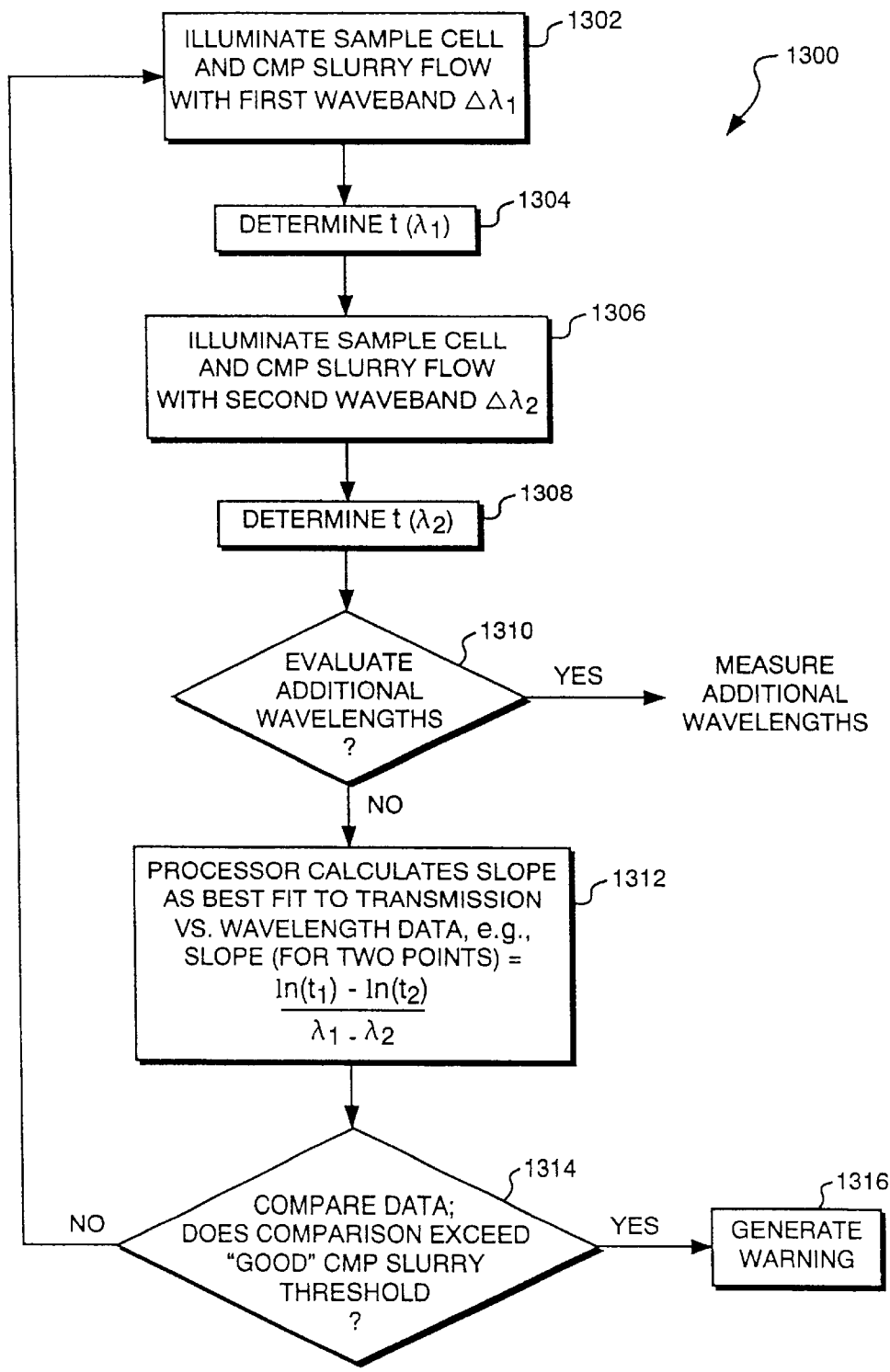

An alternative preferred embodiment of the invention directly compares a measured transmission measurement with a stored transmission measurement. Transmission values determined by system 1200 are preferably plotted with respect to wavelength, such as illustrated in FIG. 5. Specifically, the natural log of transmission values (ln(t), axis 1240) is plotted against wavelength (λ, axis 1242), as shown. Accordingly, the slope of a line C which approximates ln(transmission(λ)) at time $t_0$ may be determined, such as line $C(t_0)$. At a later time t, line C may, for example, be plotted as $C(t_0+t)$, indicating a change in the slope of ln(transmission(λ)). When the slope of line C changes by a sufficient amount, represented by angle β, determined empirically or by another measure, then the chemical content within the CMP slurry has changed and system 1200 sends a warning to manufacturing process 1224. FIG. 5 also illustrates wavelength measurement points $λ_1$, $λ_2$ used to determine the slope of line C, as known in the art. Each λ sample corresponds to a measurement point corresponding radiation passed through filter 1216, for example. Each waveband Δλ is centered about a wavelength λ such that Δλ/λ is less than approximately 5%. For example, for λ=2.5 microns, Δλ corresponds to about 0.13 microns.

Processor 1220a preferably includes solid state memory to store one or more "reference transmission" data corresponding to a preferred transmission vs. wavelength curve, or ln(t) vs. λ data, for a known CMP slurry with acceptable chemical content. The reference transmission data further includes an acceptable variance of that data from optimal where CMP slurry is deemed "acceptable." Accordingly, in this embodiment, system 1200 evaluates transmission data from flow 1210 in real-time and compares that data to reference transmission data in memory 1220a, and generates a warning when the real-time data exceeds the allowed variance, indicating an "unacceptable" CMP slurry. Memory 1220a can further include an array of curves or In(t) vs. λ data corresponding to each CMP slurry 1202a, 1202b . . . 1202m, as appropriate, such that system 1200 can operate with multiple CMP slurries used in manufacturing process 1224. A user can select which reference transmission data to use at any one time through a user interface (e.g., a keyboard) at processor 1220.

FIG. 6 shows a process flow 1300 of the invention for detecting CMP slurry quality and/or absolute chemical content. Process flow 1300 is representative for use of a system of the invention, such as illustrated in FIGS. 1 and 4. In process step 1302, the sample cell and CMP slurry flow is illuminated by radiation at a first waveband $\Delta\lambda_1$, e.g., 0.08 microns centered about 1.7 microns ($\lambda_1$). The system detector and processor then measure and determine a transmission value for $\lambda_1$, in process step 1304. In process step 1306, the sample cell and CMP slurry flow is illuminated by radiation at a second waveband $\Delta\lambda_2$, e.g., 0.03 microns centered about 0.6 microns ($\lambda_2$). The system detector and processor then measure and determine a transmission value for $\lambda_2$, in process step 1308. The systems and methods of the invention can detect further transmission values for other wavelengths and wavebands, as desired at step 1310, or calculate the slope of the transmission versus wavelength slope, as set forth in step 1312. In step 1314, the slope measured in step 1312 is measured against a reference slope stored in system memory, or alternatively, the current slope is compared to prior slope information, to evaluate change in the CMP slurry chemical content. If the slope exceeds a predetermined amount from prior slope information, or from reference slope transmission data, then a warning is generated in step 1316. Otherwise, a next set of transmission data is taken in steps 1302–1308 to evaluate CMP slurry quality over time.

The above-described optical methods and apparatus for detecting the chemical composition of a liquid are superior to analytical chemical methods and apparatus, such as titration, because they do not consume chemicals, do not create a hazardous chemical waste stream, and are much faster. With response times of 1–10 seconds, the methods and apparatus of the invention provide much better process control than do analytical chemical methods and apparatus, which have response times on the order of 30 minutes at best.

There has been described the first use of differential absorption to measure the concentration of active chemical species in CMP slurry. Further, there has been described a novel method and apparatus for extracting the chemical absorption spectral signature from a slurry transmission measurement, when this information comprises the superposition of the particle transmission, with it's own spectral signature. It should be understood that the particular embodiments shown in the drawings and described within this specification are for purposes of example and should not be construed to limit the invention which will be described in the claims below. Further, it is evident that those skilled in the art may now make numerous uses and modifications of the specific embodiments described, without departing from the inventive concepts. It is also evident that the steps recited may in some instances be performed in a different order, or equivalent structures and processes may be substituted for the various structures and processes described.

What is claimed is:

1. A system for determining the chemical content of a chemical mechanical planarization (CMP) slurry, comprising:
    a CMP sample cell having windows for passing electromagnetic radiation;
    a source of at least two wavelengths of electromagnetic radiation, one of which is strongly absorbed by said CMP slurry and the other of which is weakly absorbed by said CMP slurry;
    a detector for detecting said electromagnetic radiation and producing an electronic signal;
    optics directing said wavelengths through said sample cell and onto said detector; and
    a processor, responsive to said electronic signal, for determining a parameter representative of the chemical content of said CMP slurry.

2. A system as in claim 1 wherein said wavelengths are closely spaced.

3. A system as in claim 1 wherein said source comprises a source of three or more of said wavelength, two of which are weakly absorbed by said CMP slurry.

4. A system as in claim 1 wherein said processor comprises a computer.

5. A system as in claim 1, further comprising a memory, coupled to said processor, said memory storing instructions suitable for calculating a wavelength dependent transmission function.

6. A system as in claim 5 wherein said transmission function comprises Beer's law.

7. A system as in claim 5 wherein said memory stores instructions for calculating an optical model for wavelength dependent transmission.

8. A system as in claim 1, further comprising a memory, coupled to said processor, said memory storing instructions suitable for solving a system of three equations in three unknowns.

9. A system as in claim 1, further comprising a memory, coupled to said processor, said memory storing a reference transmission, and instructions for determining a transmission value from said signal, said reference transmission corresponding to a particular CMP slurry flow and chemical content, said memory further storing directions for directing said processor to compare said reference transmission with said transmission value.

10. A method for determining the chemical content of a CMP slurry, comprising the steps of:
    transmitting radiation through a flow of the CMP slurry, the radiation having two wavelengths, one of which is weakly absorbed by said CMP slurry and one of which is strongly absorbed by said CMP slurry;
    determining transmission of said radiation at each of the wavelengths; and
    utilizing said transmissions at said wavelengths to calculate a parameter representative of the chemical content of said CMP slurry.

11. A method as in claim 10 wherein said wavelengths are closely spaced.

12. A method as in claim 10 wherein said radiation comprises three or more of said wavelengths, two of which are weakly absorbed by said CMP slurry.

13. A method as in claim 10 wherein said utilizing comprises operating a computer.

14. A method as in claim 10 wherein said calculating comprises calculating a wavelength dependent transmission function.

15. A method as in claim 14 wherein said transmission function comprises Beer's law.

16. A method as in claim 14 wherein said calculating comprises calculating an optical model for wavelength dependent transmission.

17. A method as in claim 10 wherein said calculating comprises solving a system of three equations in three unknowns.

18. A method as in claim 10, further comprising storing a reference transmission, said calculating comprises comparing said reference transmission with said determined transmission.

19. A method for detecting chemical changes in a CMP slurry, comprising the steps of:
   transmitting radiation through a flow of the CMP slurry, the radiation having three wavelengths, one of which is weakly absorbed by said CMP slurry and two of which are strongly absorbed by said CMP slurry;
   determining transmission of said radiation at each of the wavelengths; and
   monitoring said transmission, over time, to detect chemical changes of the CMP slurry.

20. A method as in claim 19, further comprising determining a slope of transmission as a function of the wavelengths.

21. A method as in claim 20, further comprising determining a change in the logarithmic slope, overtime, the change in the slope indicating change in chemical composition of the CMP slurry.

22. A method as in claim 19 wherein said transmitting comprises utilizing a grating to select the wavelengths of the radiation.

23. A method as in claim 19 wherein said transmitting comprises using a laser.

24. A method as in claim 19 wherein said transmitting comprises utilizing at least two filters to select the wavelengths.

25. A method as in claim 19, further comprising generating a warning corresponding to the changes.

26. A method as in claim 19, further comprising storing a reference transmission and said monitoring comprises comparing said transmission to said reference transmission.

27. A method as in claim 19 wherein said monitoring comprises calculating a logarithm of transmission at each wavelength and determining a change in slope of logarithmic transmission versus wavelength.

* * * * *